US008821908B2

(12) United States Patent
Bolte et al.

(10) Patent No.: US 8,821,908 B2
(45) Date of Patent: Sep. 2, 2014

(54) MOLD-RESISTANT CONSTRUCTION MATERIALS

(75) Inventors: Andreas Bolte, Duesseldorf (DE); Stefan Frey, Deidesheim (DE); Thomas Gerke, Neuss (DE); Achim Schunk, Duesseldorf (DE); Mirko Weide, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 1453 days.

(21) Appl. No.: 11/751,890

(22) Filed: May 22, 2007

(65) Prior Publication Data

US 2007/0224250 A1    Sep. 27, 2007

Related U.S. Application Data

(63) Continuation of application No. PCT/EP2005/010758, filed on Oct. 6, 2005.

(30) Foreign Application Priority Data

Nov. 22, 2004   (DE) .................. 10 2004 056 362

(51) Int. Cl.
*A01N 25/00* (2006.01)
*A01N 25/34* (2006.01)

(52) U.S. Cl.
USPC .......................................... 424/405; 424/402

(58) Field of Classification Search
USPC ................................................ 424/405, 402
See application file for complete search history.

(56) References Cited

U.S. PATENT DOCUMENTS

| 3,632,557 | A | | 1/1972 | Brode et al. |
| 3,971,751 | A | | 7/1976 | Isayama et al. |
| 3,979,344 | A | | 9/1976 | Bryant et al. |
| 4,120,970 | A | * | 10/1978 | Bice et al. ................. 514/365 |
| 4,247,442 | A | | 1/1981 | Shimizu |
| 4,417,042 | A | | 11/1983 | Dziark |
| 4,503,210 | A | | 3/1985 | Von Au et al. |
| 4,891,400 | A | | 1/1990 | Schwabe et al. |
| 4,910,242 | A | | 3/1990 | Podola et al. |
| 4,912,153 | A | | 3/1990 | Jeremias et al. |
| 4,942,211 | A | | 7/1990 | Sommer et al. |
| 4,960,844 | A | | 10/1990 | Singh |
| 5,077,360 | A | | 12/1991 | DePompei et al. |
| 5,326,777 | A | | 7/1994 | Ludwig et al. |
| 5,378,406 | A | | 1/1995 | Nagaoka |
| 5,412,015 | A | | 5/1995 | Sommer et al. |
| 5,502,144 | A | | 3/1996 | Kuo et al. |
| 5,525,654 | A | | 6/1996 | Podola et al. |
| 5,876,738 | A | | 3/1999 | Ohno et al. |
| 5,888,415 | A | | 3/1999 | Rother et al. |
| 5,990,143 | A | | 11/1999 | Ludwig et al. |
| 6,008,290 | A | | 12/1999 | Miyoshi et al. |
| 6,025,416 | A | | 2/2000 | Proebster et al. |
| 6,162,756 | A | | 12/2000 | Friebe et al. |
| 6,184,274 | B1 | | 2/2001 | Herold et al. |
| 6,677,293 | B1 | | 1/2004 | Allgaier et al. |
| 2005/0002964 | A1 | | 1/2005 | Bockmuehl et al. |
| 2005/0009929 | A1 | | 1/2005 | Bockmuehl et al. |

FOREIGN PATENT DOCUMENTS

| CA | 1 284 854 | | 6/1991 |
| CA | 2 078 787 | | 9/1991 |
| CA | 1 294 724 | | 1/1992 |
| CA | 2 321 353 | A1 | 3/2001 |
| DE | 31 16 607 | A1 | 3/1982 |
| DE | 36 02 526 | A1 | 7/1987 |
| DE | 36 21 494 | A1 | 1/1988 |
| DE | 37 26 547 | A1 | 2/1989 |
| DE | 40 09 095 | A1 | 9/1991 |
| DE | 40 29 504 | A1 | 3/1992 |
| DE | 41 22 868 | A1 | 1/1993 |
| DE | 41 31 205 | A1 | 3/1993 |
| DE | 42 33 077 | A1 | 4/1994 |
| DE | 195 17 840 | A1 | 11/1996 |
| DE | 195 49 425 | A1 | 3/1997 |
| DE | 197 47 765 | A1 | 4/1998 |
| DE | 197 04 553 | A1 | 8/1998 |
| DE | 199 47 182 | A1 | 5/2001 |
| DE | 101 46 189 | A1 | 11/2002 |
| DE | 202004001072 | U1 | 7/2004 |
| EP | 0 118 030 | B1 | 6/1987 |
| EP | 0 370 464 | A2 | 5/1990 |
| EP | 0 254 857 | B1 | 7/1993 |
| EP | 0 316 591 | B1 | 12/1993 |
| EP | 0 327 847 | B1 | 1/1994 |
| EP | 0 552 143 | B1 | 5/1995 |
| EP | 0 824 574 | B1 | 5/1996 |
| EP | 0 881 265 | B1 | 12/1998 |
| EP | 0 931 811 | B1 | 7/1999 |
| EP | 1 035 159 | B1 | 10/2003 |
| EP | 1 094 065 | B1 | 12/2003 |
| FR | 29 02 771 | A1 | 6/2001 |
| JP | 57-018758 | A | 1/1982 |

(Continued)

OTHER PUBLICATIONS

DE 3116607 Machine translation.*
International Search Report of PCT/EP2005/010758, date Jan. 23, 2006.
Derwent Abstract XP002362273 for JP 57-018757, 1982.
Derwent Abstract XP002362274 for JP 04-122781, 1992.
Derwent Abstract XP002362275 for JP 61-016972, 1986.
"Jointing products in building construction" Sealants, DIN EN 26927, DIN Deutsches Institut fuer Normung eV., Berlin, pp. 1-5 (May 1991).

(Continued)

*Primary Examiner* — Shengjun Wang
(74) *Attorney, Agent, or Firm* — James E. Piotrowski

(57) ABSTRACT

Mold-resistant construction materials distinguished by the presence therein of an azole alone or in combination with a sporulation inhibitor and/or with a substance which is antiadhesive with respect to microorganisms.

8 Claims, No Drawings

(56) References Cited

FOREIGN PATENT DOCUMENTS

| JP | 61-016972 A | 1/1986 |
|----|-------------|--------|
| JP | 04-122781 A | 4/1992 |
| JP | 09 255400 A | 9/1997 |
| JP | 11228302 A | 8/1999 |
| JP | 2003 238301 A | 8/2003 |
| WO | 93/05089 A1 | 3/1993 |
| WO | 96/36739 A1 | 11/1996 |
| WO | 00/12660 A2 | 3/2000 |
| WO | 00/68232 A1 | 11/2000 |
| WO | 01/09249 A1 | 2/2001 |
| WO | 03/051124 A2 | 6/2003 |
| WO | 03/051125 A1 | 6/2003 |

OTHER PUBLICATIONS

"Evaluation of the action of microorganisms on plastics", DIN EN ISO 846, DIN Deusches Institut fuer Normung eV., Berlin, pp. 1-25 (Oct. 1997).
Patent Abstract of Japan, JP 09255400 (1997).
Patent Abstract of Japan, JP 2003238301 (2003).
Patent Abstract of Japan, JP 11228302 (1999).
Ullmann's Encyclopedia of Industrial Chemistry, vol. 32, Chapter 6, 8th Edition (2003).

* cited by examiner

MOLD-RESISTANT CONSTRUCTION MATERIALS

CROSS REFERENCE TO RELATED APPLICATIONS

This application is a continuation under 35 U.S.C. §365 (c) and 35 U.S.C. §120 of international application PCT/EP2005/010758, filed on Oct. 6, 2005. This application also claims priority under 35 U.S.C. §119 of DE 10 2004 056 362.4, filed on Nov. 22, 2004, which is incorporated herein by reference in its entirety.

BACKGROUND OF THE INVENTION

The present invention relates to mold-resistant construction materials and construction auxiliaries distinguished by the presence therein of an azole alone or in combination with a sporulation inhibitor and/or with a substance which is antiadhesive toward microorganisms.

Particularly when they are employed in damp areas, such as household bathrooms, shower cabinets, etc., silicone, acrylate, and other types of joint sealant frequently exhibit mold-related discolorations. These coverings, which are usually black or colored, are difficult if not impossible to remove. These affected sealants must normally then be mechanically removed and renewed. Similar comments apply to other construction materials or auxiliaries and to other materials such as filter media, textile, pelts, paper, hides or leather which are exposed to moisture and not adequately ventilated.

In order to prevent such mold coverings in the cured compositions, joint sealants are normally furnished with fungicides. An example of a fungicide used is DCOIT. The use of fungicides such as DCOIT, however, is not sufficient to keep the joint sealants durably free from mold-related discoloration. The biocides used are washed out after a relatively short time, and molds can grow on the surface of the joint sealant. A general problem here is that highly effective fungicides are washed out after a relatively short time, whereas fungicides that are not washed out so easily lack adequate activity. For other construction materials, construction auxiliaries, and the other stated materials as well it has not been possible to date to find a satisfactory solution.

EP1035159B1 describes organopolysiloxane compositions which besides organopolysiloxanes and silanes, as an antibacterial substance, comprise an iron compound and may further comprise a compound containing triazole groups.

EP0931811A1 describes organopolysiloxane compositions which besides organopolysiloxanes and silanes comprise a compound containing triazole groups and an inorganic antibacterial substance.

EP0881265A2 describes organopolysiloxane compositions which besides organopolysiloxanes and silanes comprise a compound containing triazole groups and zinc 2-pyridylthio-1-oxide.

JP2003238301 describes sealants which can comprise various combinations of fungicidal substances.

DESCRIPTION OF THE INVENTION

It was an object of the present invention, therefore, to provide for the furnishing of construction materials, construction auxiliaries, filter media, textiles, pelts, paper, and hides with substances which keep the stated fabrics and materials free from mold-related discoloration for a longer time than the fungicides used conventionally at present.

Surprisingly it has now been found that azole compounds of high concentrations are capable of fulfilling this object without the need for addition of further fungicides; tebuconazole has emerged as a particularly effective compound.

The fungicidal properties of azole compounds have already been disclosed in the prior art. For tebuconazole, the primary utility described in this context is its use in wood preservatives and in crop protection compositions, particularly for cereal growing and viniculture.

The advantageous properties and applications of azole compounds in construction materials and construction auxiliaries, as found in accordance with the invention, is not, however, anticipated by the prior art.

Furthermore, it has been found in accordance with the invention that through combination of an azole compound with a sporulation inhibitor and/or with a substance which is antiadhesive toward microorganisms it is possible to achieve a further improvement in terms of the mold-free time or discoloration-free time.

Additionally it has been found that through the use of carrier-bound forms of the stated actives, in other words of the azole compounds, the sporulation inhibitors and/or the antiadhesive substances, it is possible to achieve yet a further improvement in terms of the mold-free or discoloration-free time, silicic esters of the actives having emerged as being particularly advantageous carrier-bound forms.

The present invention accordingly provides for the use of at least one azole compound for furnishing materials selected from construction materials, construction auxiliaries, filter media, textiles, pelts, paper, hides or leather, alone or together with at least one sporulation inhibitor and/or with at least one substance which is antiadhesive toward microorganisms, the stated actives being used if desired in carrier-bound form, in particular in the form of their silicic esters, and in one preferred embodiment being used without addition of inorganic fungicides, the azole compound more preferably being the sole fungicidal compound used.

Additionally provided with the present invention, accordingly, are compositions for furnishing materials selected from construction materials, construction auxiliaries, filter media, textiles, pelts, paper, hides or leather, characterized in that they comprise at least one azole compound and also, if desired, at least one sporulation inhibitor and/or at least one substance which is antiadhesive to microorganisms, the stated actives being present if desired in carrier-bound form, in particular in the form of their silicic esters, in one preferred embodiment there being no inorganic fungicides present, and with particular preference the azole compound being the sole fungicidal compound present.

The present invention accordingly also provides materials selected from construction materials, construction auxiliaries, filter media, textiles, pelts, paper, hides or leather, characterized in that they comprise at least one azole compound and also, if desired, at least one sporulation inhibitor and/or at least one substance which is antiadhesive to microorganisms, and/or have been treated or furnished with a furnishing agent of the invention, the stated actives being used if desired in carrier-bound form, in particular in the form of the silicic esters, and in one preferred embodiment the materials being free from inorganic fungicides, and with particular preference the azole compound being the sole fungicidal compound present.

The furnishing of the paper, textiles, wall coverings, pelts, hides or leather takes place in a way which is known to the skilled worker, as for example by immersing the paper or the textiles, pelts, hides or leather into a suitably concentrated solution of a composition of the invention.

The furnishing of the filter media, construction materials or construction auxiliaries takes place, for example, by mechanical incorporation or application of a suitably concentrated solution of a composition of the invention into or to the filter media, construction materials or construction auxiliaries. The actives and solutions of the actives, preferably in organic solvents, can advantageously be applied or incorporated particularly effectively to or into such construction materials and construction auxiliaries. Retrospectively furnishing the construction materials or auxiliaries, or recharging already-furnished construction materials or auxiliaries following prolonged service, as in the case of sealants, for example, by applying the compositions of the invention is therefore possible if appropriate.

The use of azole compounds at high concentration as the sole active surprisingly of itself brings about a significant improvement in the mold-free time as compared with the fungicides that are typically used at present, such as DCOIT. A further surprise here was that, particularly with the use of tebuconazole, further-increasing mold prevention could be achieved in a virtually linear dependence with increasing concentration, whereas this was not observed when using fungicides typically used at present in sealants. This was surprising in particular since hydroxyl-containing compounds such as tebuconazole and propiconazole could have been expected to exhibit a negative effect, owing to interaction with reactive components of the sealants.

Through the use of sporulation inhibitors even as the sole active it is likewise possible to achieve the prevention or significant reduction of mold-related discoloration. The sporulation inhibitors do not kill the mold, but merely prevent the asexual reproduction of the fungus, which encompasses in particular the sporulation of the fungus and the associated unwanted discoloration, which in the majority of cases is black. Sporulation inhibitors are described for example in WO 03/051124. Those which have emerged as being particularly suitable for use in construction materials and/or construction auxiliaries, in accordance with the invention, are ortho-phenylphenol and its derivatives, in particular.

Similarly, through the use as sole actives of substances which are antiadhesive toward microorganisms it is already possible to achieve the prevention or significant reduction of mold infestation. Here, once again, the antiadhesive substances do not kill the mold, but instead prevent the mold from attaching to the materials from the outset. Antiadhesive substances are described for example in WO 03/051125. The use of nonionic surfactants in particular has emerged in accordance with the invention as being particularly suitable for use in construction materials and/or construction auxiliaries.

Through the use of carrier-bound forms of the actives it is possible to bring about what is called a retarded release effect: The active substance is provided in an inactive preliminary form and is released gradually over the course of time. As a result of the carrier, the active form is held in the formulation for longer and at the same time is protected by the carrier. The gradual release ensures that a longer-lasting effect is achieved, whereas the active free form, on account of its volatility, would escape more quickly from the formulation and at very high concentration might also possibly lead to an intense odor. Furthermore, the carrier-bound form is distinguished by the fact that, owing to its physical properties, and in particular its size, it can be incorporated more effectively into certain formulations and affixed more effectively to certain materials than can be the free form of the active substance. As a result of being bound to a carrier, moreover, it is ensured that the toxicity of the substance if used at high concentration, if appropriate, is minimized.

As a result of the inventively preferred combination of azole compounds with sporulation inhibitors and/or with antiadhesive substances and/or as a result of the use of carrier-bound forms of at least one of the stated active substances, it is possible for the advantageous properties of all of the stated classes of active to be united and thereby a synergistic effect achieved: The adhesion of mold is reduced from the outset by the antiadhesive substances; any mold which attaches in spite of this is killed by the azole compounds; and any surviving mold is hindered by the sporulation inhibitors from giving rise to unwanted coloration. Furthermore, through the use of carrier-bound forms of the active substances, the desired effects can be ensured over a prolonged time.

Azole Compound

The azole compound for use in accordance with the invention is preferably selected from azole compounds containing triazole groups and/or from propiconazole, thiobendazole and tebuconazole and/or their derivatives and/or from carrier-bound forms of the stated substances, particular preference being given to tebuconazole (a-(2-(4-chlorophenyl)ethyl)-a-(1,1-dimethylethyl)-1H-1,2,4-triazole-1-ethanol), and by derivatives there being meant mono- or polysubstituted forms of the aforementioned compounds, the substituents being selected preferably from halogen, especially fluorine, chlorine or bromine, and alkyl, especially $C_{1-6}$ alkyl, hydroxyl and alkoxy, especially $C_{1-6}$ alkoxy, and the term "azole" referring also to the salts of the azoles with organic or inorganic acids.

The azole compound is present here preferably in an amount of 0.01% to 5.0% by weight, more preferably of 0.1% to 1.0% by weight, and in particular of 0.2% to 0.6% by weight in the construction materials and construction auxiliaries. In the case of carrier-bound forms of the azole compound, the quantity figure relates to the amount of the active substance.

Sporulation Inhibitors

A sporulation inhibitor in accordance with the invention is a substance capable of preventing or at least significantly reducing the asexual reproduction of fungi, particularly of molds, the reduction in asexual reproduction not being attributable to a microbicidal or fungicidal effect. Through the use of a sporulation inhibitor rather than a microbicide, the problem of resistance developing is removed. The term "sporulation inhibitor" here also covers substances which at a higher concentration may have microbicidal or fungicidal properties but at a lower concentration, and in particular at the concentration used, inhibit the asexual reproduction of fungi, without exhibiting microbicidal or fungicidal activity.

In accordance with the invention the term "asexual reproduction" embraces, in particular, sporulation, budding, and fragmentation. By sporulation is meant the formation not only of reproductive forms, such as conidia, gonocysts, sporangiospores, arthrospores, blastospores, and their associated organs (e.g., conidiophores), but also of permanent forms (e.g., chlamydospores).

By inhibiting the sporulation of the growing fungal colonies it is possible to achieve a considerable reduction in the allergenic challenge and hence in the risk of a mold allergy, and to halt completely or retard considerably the propagation of the fungus. It is likewise possible to lessen sharply or to prevent completely the discoloration that is associated with asexual reproduction and is attributable to the sporulation. The reduction in the development of fungal spores on materials which have been furnished with the relevant substance, in comparison to materials not so furnished, is preferably more than 50%, more preferably more than 80%.

The sporulation inhibitor in this case is preferably selected from plant extracts, propolis extracts, algal extracts, fucoidin, fragrance alcohols, in particular from monoterpenes, sesquiterpenes and/or diterpenes and their derivatives, from patchouli oil, patchouli alcohol and/or its derivatives, from eugenol and/or its derivatives, from ortho-phenylphenol and/or its derivatives, and from carrier-bound forms of these substances.

Fucoidin, also known under the name fucosidan or fucoidan, is a polysaccharide from brown algae (*Fucus vesiculosa*, bladder wrack) which consists principally of sulfated L-fucose in 1,2-α-glycosidic linkage. Advantageously it has been found that the hyphal formation by *Candida albicans* is significantly reduced, while at the same time the cell growth is unaffected.

Propolis is a resinous mass having a melting point of between about 50 and 70° C. which is collected by bees and is used in the beehive as a coating on the walls and for attaching the combs. It is also known as "plugging wax", bee glue or bee resin.

The term "fragrance alcohols" refers in the context of the present invention to fragrances which possess at least one or more, preferably at least one or two, hydroxyl groups which are esterifiable or esterified, irrespective of the further structure of the molecule. Thus salicylic esters are among compounds which can be used as fragrance alcohols. In this context, all combinations of geometric isomers are suitable. It is likewise possible to use esters of these compounds, an example being anethole (1-methoxy-4-(1-propenylbenzene)) or linalyl acetate.

Particular preference is given to using fragrance alcohols having one or two free hydroxyl groups. From the large group of the fragrance alcohols which includes the terpene alcohols (which are described in more detail below), it is possible to name preferred representatives having at least one free hydroxyl group, so that in the context of the present invention the following are preferred: 10-undecen-1-ol, 2,6-dimethyl-heptan-2-ol, 2-methylbutanol, 2-methylpentanol, 2-phenyl-propanol, 2-tert-butylcyclohexanol, 3,5,5-trimethylcyclo-hexanol, 3-hexanol, 3-methyl-5-phenylpentanol, 3-octanol, 3-phenylpropanol, 4-heptenol, 4-isopropylcyclohexanol, 4-tert-butylcyclo-hexanol, 6,8-dimethyl-2-nonanol, 6-nonen-1-ol, 9-decen-1-ol, alpha-methyl-benzyl alcohol, 1-hydroxy-4-(1-propenylbenzene), amyl salicylate, benzyl alcohol, benzyl salicylate, butyl salicylate, citronellols, cyclohexyl salicylate, decanol, dihydromyrcenol, dimethyl-benzyl carbinol, dimethylheptanol, dimethyloctanol, ethyl salicylate, ethylvanillin, eugenol, heptanol, hexyl salicylate, isoeugenol, isopulegol, menthol, myrtenol, n-hexanol, nerol, nonanol, octanol, para-menthan-7-ol, phenylethyl alcohol, phenyl salicylate, tetrahydrogeraniol, tetrahydrolinalool, thymol, trans-2-cis-6-nonadienol, trans-2-nonen-1-ol, trans-2-octenol, undecanol, cinnamyl alcohol. Preference is given for example to eugenol and its derivatives, 1-hydroxy-4-(1-propenylbenzene), isoeugenol, citronellols, menthol.

Terpenes in accordance with the invention are all natural substances and derivatives that are constructed from isoprene units. Preference is given for example to farnesol, patchouli alcohol, squalene, geraniol.

In one particular embodiment the monoterpenes, sesquiterpenes and/or diterpenes or their derivatives are selected from alcohols, such as farnesol and its ethers, acids, such as farnesoic acid, and also their esters, and other monoterpenes, sesquiterpenes and/or diterpenes that carry functional groups. Both the trans isomers and the cis isomers are suitable. Likewise included are α-farnesene (3,7,11-trimethyl-1,3,6,10-dodecatetraene) and also β-farnesene (7,11-dimethyl-3-methylene-1,6,10-dodecatriene), and nerolidol (3,7,11-trimethyl-1,6,10-dodecatriene-3-ol), and also bisabolene, sesquiphellandrene, zingiberene, cadinene, aryl-tumerone, tumerone, xanthorrhizol, vulgarene, and β-selinene. Monoterpenes of preferential suitability are for example α- and β-ocimene, linalool, linalyl acetate, careens, terpineols, nerol, nerolic acid, geraniol, geranic acid, α- and β-phellandrene and/or thujone, especially geraniol, linalool and/or thujone. An example that may be given here of the diterpenes is geranylgeraniol (3,7,11,15-tetramethyl-2,6,10,14-hexadecatetraene-1-ol) and also its isomers and derivatives. It is likewise possible with preference to use plant extracts which comprise mono-, sesqui- and/or diterpenes (examples being geranium oil, rose oil, orange blossom oil, lavender oil, jasmine oil, basil oil, citronella oil, cypress oil, cedarleaf oil, coriander oil, rosewood oil, allspice oil, ginger oil or clove oil). In one particularly preferred embodiment the monoterpenes, sesquiterpenes and/or diterpenes or derivatives thereof are selected from farnesol and farnesoic acid, with farnesol being especially preferred.

Patchouli oil is obtained in accordance with the invention from the plant parts of the patchouli bush (*Pogostemon cablin* or patchouli and also *P. heyneaus*, from the family of the Laminaceae or Labiatae). In accordance with the invention it is possible to obtain the patchouli oil by extraction with solvents or mixtures thereof, preferably organic solvents, and in particular with hydrocarbons (by way of example, CAS 84238-39-1; CAS 90082-40-9).

Particular preference is given to patchouli oil obtained from the leaves by means of steam distillation (especially CAS 8014-09-3). Extraction is carried out preferentially using fermented leaves of the patchouli bush. Patchouli oil is particularly effective at attaching to surfaces, thereby allowing the furnishing of textiles in particular, but also of plastics and metal surfaces, to be carried out particularly effectively and simply. The patchouli oil obtained by steam distillation of the fermented leaves contains, in addition to patchouli alcohol, patchoulenol, patchoulenone, norpatchoulenol, nortetrapatchoulol, seychellene, α-patchoulene, β-patchoulene, α-guaiene, and α-bulnesene.

Of patchouli alcohol it is possible to use all of the configurational isomers, though particular preference is given to the naturally occurring (−)-patchouli alcohol. By derivatives of patchouli alcohol are meant in particular, as well as esters and ethers of patchouli alcohol, patchoulenol, norpatchoulenol, and seychellene.

In accordance with the invention, eugenol is 4-allyl-2-methoxy-phenol. The derivatives of eugenol preferably include esters and ethers of eugenol which form by reaction with the phenolic hydroxyl group. Particular mention may be made here of the eugenol ethers, eugenol benzoate, eugenol palmitate, eugenol cinnamate, and eugenol acetate (aceteugenol). Likewise suitable is eugenol-O-D-glucopyranoside (citrusin C). Eugenol is particularly preferred.

The derivatives of ortho-phenylphenol preferably include esters and ethers of ortho-phenylphenol which are formed by reaction with the phenolic hydroxyl group. The carboxylic acid radical of the ortho-phenylphenol ester may in particular be a $C_{1-18}$ alkyl-carboxylic acid, preferably a $C_{1-12}$ carboxylic acid, or a $C_{6-10}$ aryl-$C_{1-6}$ alkyl-carboxylic acid, it being possible for the alkyl radical to be branched or unbranched and saturated or unsaturated. The alcohol radical of the ortho-phenylphenol ether may in particular be a $C_{1-18}$ alcohol, preferably a $C_{1-6}$ alcohol. In accordance with the invention the derivatives of ortho-phenylphenol likewise include mono- or poly-, in particular mono-, di- or tri-, substituted ortho-phenylphenol, mono- or poly-, in particular mono-, di- or trisubstituted ortho-phenylphenol ethers and ortho-phenylphenol esters, and also mono- or polysubstituted, especially mono-, di- or trisubstituted, biphenyl. The substituents in this case are preferably selected from the group consisting of $C_{1-6}$ alkyl, $C_{1-6}$ alkoxy, $C_{6-10}$ aryl, $C_{6-10}$ aryl-$C_{1-6}$ alkyl, $C_{6-10}$ aryl-$C_{1-6}$ alkoxy, hydroxyl, halogen, especially chlorine or fluorine, nitro, cyano, amino, mono- and di-$C_{1-6}$ alkylamino, and benzyl. Mention may be made here in particular of ortho-phenylphenol benzoate, ortho-phenylphenol palmitate, ortho-phenylphenol cinnamate, ortho-phenylphenol acetate, and ortho-phenylphenol-O-β-D-glucopyranoside.

In one embodiment which is particularly preferred in accordance with the invention the sporulation inhibitor is ortho-phenylphenol and/or an ortho-phenylphenol silicic ester.

The concentration of sporulation inhibitors used to inhibit the asexual reproduction of fungi in the compositions of the invention can be varied by the skilled worker within a broad range, depending on the conditions of use of the compositions.

The sporulation inhibitor is used preferably in an amount of 0.00001% to 1% by weight, more preferably in an amount of 0.0001% to 0.1% by weight, and particularly in an amount of 0.001% to 0.05% by weight. In the case of carrier-bound forms of the sporulation inhibitor, the quantity figure relates to the amount of the active substance.

Antiadhesive Substances

An antiadhesive substance in accordance with the invention is a substance capable of producing the attachment of microorganisms, particularly of fungi, and especially of molds, the antiadhesive effect preferably being not attributable to a microbicidal or fungicidal effect. Through the use of an antiadhesive substance rather than a microbicide, therefore, the problem of development of resistance is removed. The reduction of the attachment of microorganisms to materials which have been furnished with the substance in question, in comparison to materials not so furnished, is preferably more than 50%, more preferably more than 80%.

An antiadhesive substance in this context also includes substances which at higher concentration may have microbicidal or fungicidal properties but at a lower concentration, and in particular at the concentration employed, inhibit the attachment of microorganisms or fungi without exhibiting microbicidal or fungicidal activity.

In the case of fungi the antiadhesive action here may be attributable to an effect on the morphogenesis of the fungi.

The term "morphogenesis" refers to the development of specific cellular forms of fungi, such as of hyphae, spores (in the sense of permanent forms or propagation cells) or their associated organs (e.g., conidiophores). These different forms of fungal cells are easily recognized either macroscopically or microscopically. The different cellular forms differ in their adhesion properties to tissue, textiles, etc.

By influencing is meant, in the sense of the invention, not only the inhibition of the transition from a better-adhering to a less well-adhering cellular form but also the preference or preferred development of a less well-adhering cellular form over a better-adhering form.

The antiadhesive substance is preferably selected here from plant extracts, propolis extracts, algae extracts, fucoidin, fragrance alcohols, especially from monoterpenes, sesquiterpenes and/or diterpenes and their derivatives, from patchouli oil, patchouli alcohol and/or its derivatives, from eugenol and/or its derivatives, from dispirotripiperazine compounds and/or derivatives thereof, from nonionic surfactants and/or derivatives thereof, and also from coupled or carrier-bound forms of these substances.

Illustrative information on plant extracts, propolis extracts, algae extracts, fucoidin, fragrance alcohols, especially on monoterpenes, sesquiterpenes and/or diterpenes and their derivatives, on patchouli oil, patchouli alcohol and/or its derivatives and also on eugenol and/or its derivatives has already been given earlier on above, particularly in respect of preferred embodiments. The remarks apply here correspondingly.

The derivatives of dispirotripiperazine that can be used in accordance with the invention are preferably compounds of the general formula (I)

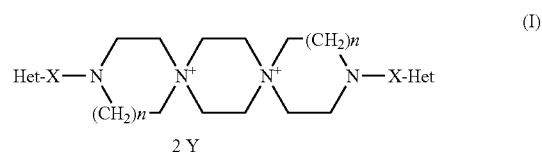

where n is 1 or 2,
X is a direct bond, NH, or a methylene group,
Het is a substituted (C5-C6)-heteroaryl radical having one to three, in particular two, heteroatoms, the heteroatoms being selectable in particular from N, O and S, it also being possible for the heteroaryl radical to be mono- or polysubstituted, in particular mono-, di- or trisubstituted, in particular by radicals selected from the group consisting of (C1-C6) alkyl, (C1-C6) alkylthio, amino, mono- or di-(C1-C6) alkylamino, hydroxyl, trifluoromethyl, phenyl, styryl, nitro, CHO, COOH, CN, pyrrolidino, piperazino, cyano, isocyano, thiocyano, isothiocyano, and halogen.

Het here is preferably a pyrimidinyl radical, especially a pyrimidin-6-yl radical of the formula (II)

where R1 is preferably (C1-C6) alkylthio, especially methylthio, R2 is preferably halogen, especially chlorine, and R3 is preferably nitro.

With particular preference the dispirotripiperazine derivatives comprise an N,N'-bis(4-halo-2-alkylthio-5-nitropyrimidinyl) derivative, and especially N,N'-bis(4-chloro-2-methylthio-5-nitropyrimidinyl)dispirotripiperazine.

Nonionic surfactants used are preferably alkoxylated, advantageously ethoxylated or propoxylated, especially primary, alcohols having preferably 8 to 22 C atoms, in particular 8 to 18 C atoms, and on average 1 to 20, preferably 1 to 12, mol of alkylene oxide or 5 to 15 mol of alkylene oxide, preferably ethylene oxide (EO), per mole of alcohol, in which the alcohol radical may be linear or, preferably, methyl-branched in position 2 and/or may comprise linear and methyl-branched radicals in a mixture, such as are typically present in oxo-process alcohol radicals. In particular, however, preference is given to alcohol ethoxylates with linear radicals from alcohols of natural origin having 12 to 18 C atoms, e.g., from coconut, palm, tallow fatty or oleyl alcohol, and on average 2 to 8 or 5 to 15 EO per mole of alcohol. The preferred ethoxylated alcohols include for example $C_{12-14}$ alcohols with 3 EO or 4 EO, $C_{9-11}$ alcohol with 7 EO, $C_{13-15}$ alcohols with 3 EO, 5 EO, 7 EO or 8 EO, $C_{12-18}$ alcohols with 3 EO, 5 EO or 7 EO, and mixtures of these, such as mixtures of $C_{12-14}$ alcohol with 3 EO and $C_{12-18}$ alcohol with 5 EO. The stated degrees of ethoxylation represent average values, which for a specific product may be an integral or a fractional number. Preferred alcohol ethoxylates have a narrowed homologue distribution (narrow range ethoxylates, NREs). Additionally to these nonionic surfactants it is also possible to use fatty alcohols having more than 12 EO. Examples thereof are tallow fatty alcohol having 14 EO, 25 EO, 30 EO or 40 EO.

Suitable nonionic surfactants further include substances which are commonly known to the skilled worker as nonionic emulsifiers. The nonionic surfactants in this sense contain as a hydrophilic group, for example, a polyol group, a polyether group, a polyamine or a polyamide group or a combination of said groups. Examples of such compounds are $C_8$-$C_{22}$ alkyl-mono- and -oligoglycosides and their ethoxylated analogues, adducts of 2 to 30 mol of ethylene oxide and/or 0 to 5 mol of propylene oxide with linear fatty alcohols having from 8 to 22 C atoms, with fatty acids having 12 to 22 C atoms, and with alkylphenols having 8 to 15 C atoms in the alkyl group, $C_{12}$-$C_{22}$ fatty acid monoesters and diesters of adducts of 1 to 30 mol of ethylene oxide with glycerol, and also adducts of 5 to 60 mol of ethylene oxide with castor oil and with hydrogenated castor oil.

It is also possible to use low-foaming nonionic surfactants which contain alternating ethylene oxide and alkylene oxide units. Of these, preference is given in turn to surfactants having EO-AO-EO-AO blocks, with in each case one to ten EO or AO groups attached to one another before a block of the other respective groups follows. Examples thereof are surfactants of the general formula

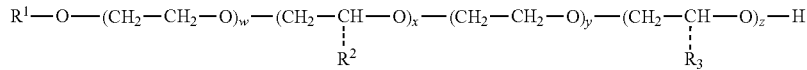

in which $R^1$ is a straight-chain or branched, saturated or mono- or polyunsaturated $C_{6-24}$ alkyl or alkenyl radical; each group $R^2$ or $R^3$ independently of one another is selected from —$CH_3$; —$CH_2CH_3$, —$CH_2CH_2$—$CH_3$, $CH(CH_3)_2$, and the indices w, x, y, and z independently of one another are integers from 1 to 6. They can be prepared by known methods from the corresponding alcohols $R^1$—OH and ethylene oxide and/or alkylene oxide. The radical $R^1$ in the above formula may vary according to the provenance of the alcohol. If natural sources are used, the radical $R^1$ has an even number of carbon atoms and is generally unbranched, with preference being given to the linear radicals from alcohols of natural origin having 12 to 18 C atoms, such as from coconut, palm, tallow fatty or oleyl alcohol. Examples of alcohols obtainable from synthetic sources are the Guerbet alcohols or radicals methyl-branched in position 2, or linear and methyl-branched radicals, such as are typically present in oxo-process alcohol radicals. Irrespective of the nature of the alcohol used to prepare the nonionic surfactants present in accordance with the invention in the compositions, preference is given to compositions of the invention in which $R^1$ in the formula above is an alkyl radical having 6 to 24, preferably 8 to 20, more preferably 9 to 15, and in particular 9 to 11 carbon atoms. As a suitable alkylene oxide unit which may be present in alternation with the ethylene oxide unit in the nonionic surfactants, as well as propylene oxide, butylene oxide is particularly suitable. However, suitability is also possessed by further alkylene oxides, in which $R^2$ and $R^3$ independently of one another are each selected from —$CH_2$—$CH_2$—$CH_3$ and $CH(CH_3)_2$.

Further suitable nonionic surfactants are nonionic block copolymers of the kind described for example in WO 00/12660, fully incorporated here by reference. These may be, for example, AB, AA'B, ABB', ABA' or BAB' block copolymers, with A and A' standing for the hydrophilic block and B and B' for a hydrophobic block. The blocks A and A', independently of one another, may for example be a polyalkylene oxide, in particular a polypropylene oxide or polyethylene oxide, a polyvinylpyridine, polyvinyl alcohol, polymethyl vinyl ether, polyvinylpyrrolidine or a polysaccharide. The blocks B and B' may independently of one another be for example an optionally substituted alkyl radical, which can be obtained for example by polymerizing units selected from the group consisting of 1,3-butadiene, isoprene, all constitutional isomers of dimethylbutadiene, 1,3-pentadiene, 2,4-hexadiene, α-methylstyrene, isobutylene, ethylene, propylene or styrene, or mixtures thereof. The molecular weights of the blocks A, A', B, and B' are preferably, independently of one another, between 500 and 50,000 g/mol. In accordance with the invention preferably at least one of the blocks A and A' is an alkylene oxide.

A further class of nonionic surfactants employed with preference, which are used either as sole nonionic surfactant or in combination with other nonionic surfactants, are alkoxylated, preferably ethoxylated, or ethoxylated and propoxylated, fatty acid alkyl esters, preferably having 1 to 4 carbon atoms in the alkyl chain, especially fatty acid methyl esters.

Moreover, as nonionic surfactants, it is also possible to use alkyl-glycosides of the general formula $RO(G)_x$, in which R is a primary straight-chain or methyl-branched aliphatic radical, especially an aliphatic radical methyl-branched in position 2, having 8 to 22, preferably 12 to 18, C atoms, and G is a glycose unit having 5 or 6 C atoms, preferably glucose. The degree of oligomerization, x, which indicates the distribution of monoglycosides and oligoglycosides, is any number between 1 and 10; preferably x is 1.2 to 1.4.

Nonionic surfactants of the amine oxide type, examples being N-cocoalkyl-N,N-dimethylamine oxide and N-tallow-alkyl-N,N-dihydroxyethyl-amine oxide, and of the fatty acid alkanolamide type may also be suitable.

Further suitable surfactants are polyhydroxy fatty acid amides of the following formula

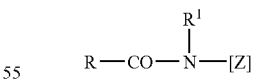

in which RCO is an aliphatic acyl radical having 6 to 22 carbon atoms, $R^1$ is hydrogen or an alkyl or hydroxyalkyl radical having 1 to 4 carbon atoms, and [Z] is a linear or branched polyhydroxyalkyl radical having 3 to 10 carbon atoms and 3 to 10 hydroxyl groups. The polyhydroxy fatty acid amides are known compounds which are typically obtainable by reductive amination of a reducing sugar with ammonia, an alkylamine or an alkanolamine, and subsequent acylation with a fatty acid, a fatty acid alkyl ester or a fatty acid chloride.

The group of the polyhydroxy fatty acid amides also includes compounds of the formula

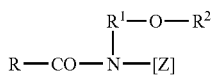

in which R is a linear or branched alkyl or alkenyl radical having 7 to 12 carbon atoms, $R^1$ is a linear, branched or cyclic alkyl radical or an aryl radical having 2 to 8 carbon atoms, and $R^2$ is a linear, branched or cyclic alkyl radical or an aryl radical or an oxyalkyl radical having 1 to 8 carbon atoms, preference being given to $C_{1-4}$ alkyl or phenyl radicals, and [Z] represents a linear polyhydroxyalkyl radical whose alkyl chain is substituted by at least two hydroxyl groups, or represents alkoxylated, preferably ethoxylated or propoxylated, derivatives of said radical.

[Z] is preferably obtained by reductive amination of a reduced sugar: for example glucose, fructose, maltose, lactose, galactose, mannose or xylose. The N-alkoxy- or N-aryloxy-substituted compounds can then be converted into the desired polyhydroxy fatty acid amides by reaction with fatty acid methyl esters in the presence of an alkoxide catalyst.

Further nonionic surfactants which can be used are the endgroup-capped poly(oxyalkylated) surfactants of the formula

in which $R^1$ and $R^2$ are linear or branched, saturated or unsaturated, aliphatic or aromatic hydrocarbon radicals having 1 to 30 carbon atoms, $R^3$ is H or a methyl, ethyl, n-propyl, isopropyl, n-butyl, 2-butyl or 2-methyl-2-butyl radical, x stands for values between 1 and 30, k and j stand for values between 1 and 12, preferably between 1 and 5. If x is =2, each $R^3$ in the above formula can be different. $R^1$ and $R^2$ are preferably linear or branched, saturated or unsaturated, aliphatic or aromatic hydrocarbon radicals having 6 to 22 carbon atoms, particular preference being given to radicals having 8 to 18 C atoms. For the radical $R^3$, H, —$CH_3$ or —$CH_2CH_3$ are particularly preferred. Particularly preferred values for x lie in the range from 1 to 20, in particular from 6 to 15.

In one particularly preferred embodiment the nonionic surfactants comprise an adduct of alkylene oxide units, especially ethylene oxide (EO) and/or propylene oxide (PO) units, with alkylphenols, the alkyl radical of the alkylphenol comprising preferably between 6 and 18 C atoms, more preferably between 6 and 12 C atoms, especially 8, 9 or 10 C atoms, and there being preferably between 1 and 18 ethylene oxide (EO) units, more preferably between 5 and 15 EO units, especially 8, 9 or 10 EO units, adducted to the alkylphenol radical, the stated values being average values and it being possible for the alkyl radical of the alkylphenol to be linear or to be methyl-branched in position 2, or for linear and methyl-branched radicals to be present in a mixture, of the kind typically present in oxo-process alcohol radicals. In one particularly preferred embodiment the nonionic surfactant is an adduct of on average 9 EO units with nonylphenol, the alkyl radical and the polyethylene radical preferably being positioned meta to one another. A product of this kind is available, for example, under the name Disponil NP9 (Cognis, Germany).

In a further particularly preferred embodiment the non-ionic surfactant is an adduct of ethylene oxide (EO) units with a fatty alcohol comprising preferably between 10 and 22 C atoms, more preferably between 14 and 20 C atoms, in particular between 16 and 18 C atoms, there being preferably between 4 and 24, more preferably between 10 and 22, EO units, in particular 11, 12, 13, 19, 20 or 21 EO units, adducted with the fatty alcohol. Preferred products composed of a $C_{16-18}$ alcohol with 12 or 20 EO units are available for example under the trade name Eumulgin B1 or Eumulgin B2, respectively (Cognis, Germany).

In a further particularly preferred embodiment the non-ionic surfactant is an adduct of ethylene oxide (EO) units with a fatty alcohol comprising preferably between 8 and 22 C atoms, more preferably between 10 and 20 C atoms, in particular between 12 and 18 C atoms, there being preferably between 3 and 15, more preferably between 5 and 11, EO units, in particular 6, 7, 8, 9 or 10 EO units, adducted with the fatty alcohol. Preferred products composed of a $C_{12-18}$ alcohol with 7 or 9 EO units are available for example under the trade name Dehydol LT7 and Dehydol 100, respectively (Cognis, Germany).

In a further particularly preferred embodiment the non-ionic surfactant is an adduct of ethylene oxide (EO) units with a fatty alcohol comprising preferably between 18 and 26 C atoms, more preferably between 20 and 24 C atoms, in particular 22 C atoms, there being preferably between 6 and 16, more preferably between 8 and 12, EO units, in particular 9, 10 or 11 EO units, adducted with the fatty alcohol. A preferred product composed of a $C_{22}$ alcohol with 10 EO units is available for example under the trade name Mergital B10 (Cognis, Germany).

In a further particularly preferred embodiment the non-ionic surfactant is an adduct of ethylene oxide (EO) and propylene oxide (PO) units with a fatty alcohol comprising preferably between 6 and 18 C atoms, more preferably between 10 and 16 C atoms, in particular between 10 and 12 or between 12 and 14 C atoms, there being preferably between 1 and 10, more preferably between 3 and 7, in particular 4, 5 or 6, EO units and also preferably between 1 and 10, more preferably between 2 and 6, in particular 3, 4, 5 or 6, PO units adducted with the fatty alcohol. In one preferred embodiment this nonionic surfactant is a block copolymer in which preferably the EO units are adducted with the fatty alcohol and the PO units follow the EO units, it being possible for the alkyl radical of the fatty alcohol to be linear or methyl-branched in position 2 or to comprise linear and methyl-branched radicals in a mixture, of the kind typically present in oxo-process alcohol radicals. A preferred product which is composed of a $C_{12}$-$C_{14}$ alcohol with 5 EO and 4 PO units is available for example under the name Dehypon LS 54 (Cognis, Germany). A further preferred product which is composed of a $C_{10-12}$ alcohol with 5 EO and 5 PO units is available for example under the name Biodac 2/32 (Cognis, Germany).

In a further embodiment preferred in accordance with the invention the nonionic surfactant is a fluorinated or fluorine-containing nonionic surfactant. Particular preference is given in this context to an adduct of alkylene oxide units, especially ethylene oxide (EO) and/or propylene oxide (PO) units, with an alkyl alcohol, the alkyl alcohol comprising preferably between 4 and 20 C atoms, more preferably between 6 and 18 C atoms, and there being preferably between 1 and 18, more preferably between 2 and 16, EO units adducted to the alkyl alcohol; the compound, preferably the alkyl radical, contains at least one fluorine atom, preferably at least 5 fluorine atoms, in particular between 5 and 30 fluorine atoms. In one particularly preferred embodiment the compound or mixture of compounds is one having the formula $F(CF_2F_2)_{1-7}CH_2CH_2O(CH_2CH_2O)_{1-15}H$. A nonionic surfactant of this kind is available for example under the name Zonyl FSO 100 (Du-Pont, France).

The hydroxyl groups of the aforementioned hydroxyl-bearing nonionic surfactants may in one particular embodiment, in accordance with the invention, also be partly or fully etherified or esterified. This may in particular involve an ether bond to a $C_{1-6}$ alkyl group, preferably to a methyl, ethyl, isopropyl or tert-butyl group. Among the ester bonds, preference is given to those to a $C_{1-6}$ alkanecarboxylic acid, in particular to acetic acid or maleic acid.

The antiadhesive substance is preferably a nonionic surfactant, more preferably Eumulgin B1 and/or an Eumulgin B1 silicic ester.

The antiadhesive substance is used preferably in an amount of 0.001% to 10% by weight, more preferably of 0.01% to 2.0% by weight, in particular in an amount of 0.05% to 1.0% by weight. In the case of carrier-bound forms of the antiadhesive substance, the quantity figure refers to the amount of the active substance.

Carrier-Bound Actives

One preferred embodiment uses at least one active selected from azole compounds, sporulation inhibitors, and antiadhesive substances in carrier-bound form. Carriers suitable in this context include, in particular, molecules which permit covalent binding and/or intercalative binding of the actives. Examples of the first kind of carriers include macromolecular molecules with an acid function, which permit the binding of hydroxyl-containing actives in the form of ester bonds. Examples of the second kind of carriers include what are called cage molecules, which allow the accommodation of the actives into the cage structure.

As esters of the actives, i.e., of the azoles, of the sporulation inhibitors and/or of the antiadhesive substances, it is particularly preferred to use those with silicic acids according to formulae I and II. The preparation of the silicic esters is accomplished in particular by simple transesterification of silicic esters (n=1) or oligosilicic esters (n>1) of lower alcohols with the stated actives. Depending on the reaction time and reaction conditions, the lower alcohols are eliminated and the desired actives are bound, the alcohols along the Si—O—Si chain being replaced more easily than the terminal alcohols.

Preference is given to using silicic esters of one of the formulae, (I) or (II), and/or mixtures thereof.

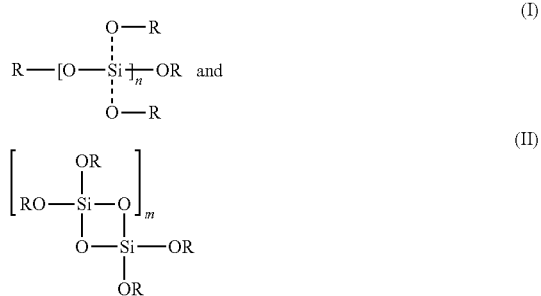

where at least one R is the active substance, in other words alternatively an azole compound, a sporulation inhibitor or an antiadhesive substance, and all of the other Rs, independently of one another, are selected from the group containing H, the straight-chain or branched, saturated or unsaturated, substituted or unsubstituted $C_{1-6}$ hydrocarbon radicals, terpene alcohols, and polymers, with m adopting values from the range 1 to 20 and n adopting values from the range 1 to 100.

According to a further preferred embodiment at least two or three radicals R are the active substance, in other words alternatively an azole compound, a sporulation inhibitor or an antiadhesive substance.

The degrees of oligoimerization "n" of the silicic esters of the invention are preferably between 1 and 20. In particularly preferred compounds, n adopts values between 1 and 15, in particular between 1 and 12, and especially between 1 and 10, more particularly the values 4, 5, 6, 7 or 8.

The silicic esters used in accordance with the invention are notable for high stability to hydrolysis and can be used even in aqueous media or in production operations for granules, sealants, etc., without suffering excessive losses in activity. As a result, the release of the active from the materials of the invention takes place slowly and in comparatively small amounts, so that over a relatively long period of time there is continuous gradual release of the actives from the products.

According to one particularly preferred embodiment there may be one or more polymer radicals on the silicic esters. To prepare the silicic esters it is preferred to use those polymers which contain free hydroxyl groups. In particular the polymer radical or radicals are selected from starch and/or its derivatives, cellulose and/or its derivatives, polyvinyl alcohol, polyols, hydroxy-polydimethylsiloxanes (especially α,ω-dihydroxypolydimethylsiloxanes), and polyphenols, especially polyvinyl alcohol. It is particularly preferred for there to be a polymer radical on the active-carrying silicic esters. For use in sealants it is particularly preferred to employ more short-chain polymers.

This specific embodiment has the advantage that the silicic esters can be individually tailored, depending on the field of application, to the target application and/or to the circumstances of application. By way of example, particularly suitable polymers are those which improve the ease of incorporation of the materials, increase the adhesion, particularly to surfaces, and influence the release properties in a desired manner.

Furthermore, it is also possible to use esters of the inventive azole compounds, sporulation inhibitors and/or antiadhesive substances with polymers. For these materials as well, the result is greater ease of adaptation to the target application, such as improved attachment or adhesion to surfaces, for example, or more favorable conditions for incorporability. The hydrolysis of this ester compound, as on repeated contact with water, for example, releases the actives slowly, and they can then develop their activity.

Materials of this kind are realized with particular preference by reacting the active with polymers which carry functional groups which are selected in particular from acid groups, acid chloride groups, ester groups, and primary, secondary and tertiary amide groups.

As polymers it is more preferred in accordance with the invention to use polyacrylic acid, polyacrylic esters, polymethacrylic acid, polymethacrylic esters, polycarboxylic acids (especially carboxymethylcellulose), and copolymers of the parent monomer (including those with monomers other than the stated monomers) and primary, secondary or tertiary polyacrylamides. Particularly preferred chain lengths in this context are from approximately 2000 to 300 000 g/mol.

According to a further preferred embodiment the polymer ester is prepared by reacting the active with monomers or polymers which carry one or more isocyanate groups. The urethanes which are produced by the reaction of an alcohol function with an isocyanate group undergo hydrolysis slowly, again, and release the active controlledly.

Preference is given to using monomeric, aliphatic or aromatic mono-, di- and/or triisocyanates. The resultant urethanes or polyurethanes (when using isocyanates having two or more isocyanate groups) are likewise able to undergo hydrolysis and to release the actives slowly.

Preferred monoisocyanates are for example the linear or branched aliphatic monoisocyanates having 6 to 44 C atoms, examples being hexyl isocyanate, heptyl isocyanate, octyl isocyanate, nonyl isocyanate, decyl isocyanate, undecyl isocyanate, dodecyl isocyanate, tridecyl isocyanate, quatadecyl isocyanate, pentadecyl isocyanate, hexadecyl isocyanate, heptadecyl isocyanate, octadecyl isocyanate, and the corresponding higher homologues of this series. Likewise preferred are aromatic monoisocyanates such as phenyl isocyanate, benzyl isocyanate or biphenylyl isocyanate.

Preferred diisocyanates $(Q(NCO)_2)$ are in particular those in which Q is selected from an aliphatic, optionally substituted hydrocarbon radical having 4 to about 15 carbon atoms, an aromatic, optionally substituted hydrocarbon radical having 6 to about 15 carbon atoms or an optionally substituted araliphatic hydrocarbon radical having 7 to about 15 carbon atoms. Mention may be made here, by way of example, of tetramethylene diisocyanate, hexamethylene diisocyanate, dodecamethylene diisocyanate, dimer fatty acid diisocyanate, 1,4-diisocyanatocyclohexane, 1-isocyanato-3,3,5-trimethyl-5-isocyanatomethylcyclohexane (IPDI), 4,4'-diisocyanatodicyclohexylmethyl, 2,2-bis(4-isocyanatocyclohexyl) propane, 1,3- and 1,4-diisocyanatobenzene, 2,4- or 2,6-diisocyanatotoluene or their mixtures, 2,2'-, 2,4 or 4,4'-diisocyanatophenylmethane, tetramethylxylylene diisocyanate, p-xylylene diisocyanate, and mixtures of these compounds.

Particularly preferred are toluene diisocyanate, hexamethylene diisocyanate, and meta-tetramethylxylylene diisocyanate.

Triisocyanates that are suitable are principally aromatic triisocyanates such as, for example, tris(p-isocyanatophenyl) thiophosphate, triphenylmethane 4,4',4''-triisocyanate, and, in particular, the various isomeric trifunctional homologues of diphenylmethane diisocyanate (MDI).

Also suitable as triisocyanates are adducts of diisocyanates and low molecular weight triols, especially the adducts of aromatic diisocyanates and triols such as trimethylolpropane or glycerol, for example. These adducts too are subject to the abovementioned restrictions on the diisocyanate content and also on the amount of polyisocyanates having a functionality >3.

Aliphatic triisocyanates such as, for example, the biuretization product of hexamethylene diisocyanates (HDI) or the isocyanuratization product of HDI, or else the same trimerization products of isophorone diisocyanate (IPDI), are also suitable for the compositions of the invention.

Polyisocyanates are the dimerization or trimerization products of the diisocyanates already stated above as being preferred. Examples of suitable isocyanates are the dimerization or trimerization products of the diisocyanates 2,4-tolylene diisocyanate (2,4-TDI), 2,6-tolylene diisocyanate (2,6-TDI), or a mixture of said isomers, 2,2'-diphenylmethane diisocyanate (2,2'-MDI), 2,4'-diphenylmethane diisocyanate (2,4'-MDI), 4,4'-diphenylmethane diisocyanate (4,4'-MDI), 1,5-naphthylene diisocyanate (NDI), 1,4-phenylene diisocyanate, 1,3-tetramethylxylylene diisocyanate (TMXDI), hydrogenated MDI (HMDI), isophorone diisocyanate (IPDI), hexamethylene 1,6-diisocyanate (HDI), 2-isocyanatopropylcyclohexyl isocyanate (IPCI), 2-butyl-2-ethyl-pentamethylene diisocyanate (BEPDI), lysine diisocyanate (LDI), 1,12-dodecyl diisocyanate, cyclohexyl 1,3- or 1,4-diisocyanate, 2-methylpentamethylene diisocyanate (MPDI) or the like, containing for example urethane, allophanate, urea, biuret, uretidone, carbidiimide or ketonimine groups of the kind formed by dimerization or trimerization of the abovementioned diisocyanates. Particularly suitable are oligomeric or polymeric compounds carrying isocyanate groups, of the kind produced, for example, during isocyanate preparation or of the kind which remain as residual products in the distillation bottoms when distilling crude isocyanate products. Examples of materials particularly suitable in this context are crude MDI, as obtainable directly after the preparation of MDI, and polymeric MDI, as remains in the distillation bottoms after the distillation of MDI from the crude MDI.

It is preferred to add an appropriate amount of active to the monomers and so to produce corresponding monomers. For instance it is possible to produce materials which, depending on the monomers used (monoisocyanate, diisocyanates, triisocyanates or polyisocyanates), carry one or more, in particular one, two or three, releasable actives. It is also possible here, via a polymerization reaction, to produce a polymer chain having terminal radicals of active.

Monomers or polymers of this kind, in sealants for example, can be used directly in the cartridge or in a separate compartment, as additives. It is likewise possible to add the corresponding actives directly to the monomers of the sealants during the sealants' production, particularly in the case of urethane-based sealants. The use of the reaction products of mono-, di- and/or triisocyanates with the corresponding actives in sealants is particularly preferred.

Suitable chain extenders, which can be used additionally in the context of a polymerization reaction for preparing the materials for use in accordance with the invention, include, for example, polyhydric alcohols such as ethylene glycol, propylene glycol, propane-1,3-diol, butane-1,4-diol, hexane-1,6-diol, trimethylolpropane, glycerol, pentaerythritol, sorbitol, mannitol or glucose. Also low molecular mass polyester diols such as bis(hydroxyethyl) succinate, glutarate or adipate, or a mixture of two or more of them, or low molecular mass diols containing ether groups, such as diethylene glycol, triethylene glycol, tetraethylene glycol, dipropylene glycol, tripropylene glycol or tetrapropylene glycol, can be used as well. Likewise suitable are amines such as ethylenediamine, hexamethylenediamine, piperazine, 2,5-dimethyl-piperazine, 1-amino-3-aminomethyl-3,5,5-trimethylcyclohexane (isophorone-diamine, IPDA), 4,4'-diaminodicyclohexyl-methane, 1,4-diaminocyclohexane, 1,2-diaminopropane, hydrazine, hydrazine hydrate, amino acid hydrazides such as 2-aminoacetic hydrazide or bishydrazides such as succinic bishydrazide. The accompanying use, in small fractions, of compounds having a functionality of three or more with respect to an isocyanate polyaddition reaction is also possible in order to achieve a certain degree of branching, as is the aforementioned possibility of using trifunctional or higher polyfunctional polyisocyanates for the same purpose. Monohydric alcohols such as n-butanol or n-dodecanol and stearyl alcohol can be used accompanyingly in small amounts.

In one inventively preferred embodiment at least one of the active substances selected from azole, sporulation inhibitor, and antiadhesive substance is present in an above-described esterified form, preferably in the form of a silicic ester.

Cage molecules in the context of the invention are, in particular, those organic macrocyclic molecules which have a cagelike three-dimensional structure and which, as "host" molecules, are capable of containing as inclusions one or more "guest" molecules. Preferably only one guest molecule is included in each case.

In this case the purposive slow release of the active substances can take place via equilibrium setting from (frequently noncovalent) binding or by complexation of the compound from a cage molecule.

Owing to the relatively hydrophobic outer shell of the cage substances, it is particularly easy to incorporate the loaded cage molecules into the products of the invention, particularly into those having a relatively hydrophobic character.

One particularly great advantage of the use of cage molecules is that it is possible after a prolonged time to replace the substances in the products that have diffused out, by reloading the cage molecules. Concentrated solutions of the stated actives are especially suitable for this purpose. In this context it is likewise possible to produce products which do not contain the free actives in complexed or bound form in the cage molecules from the outset, but instead which are loaded with these actives only when in the application situation. This is sensible in formulation terms for fields of use that are known to the skilled worker.

As organic cage molecules mention may be made of cucurbiturils, calixarenes, calixresorcarenes, cyclodextrins, cyclophanes, crown ethers, fullerenes, cryptophanes, carcerands, hemicarcerands, cyclotriveratrylenes, spherands, and cryptands.

Particularly preferred in accordance with the invention are the cucurbiturils, calixarenes, and calixresorcarenes, especially cucurbiturils.

Cucurbiturils and their preparation are described in the literature, as for example in WO 00/68232 and EP-A 1 094 065, and also the further references cited therein. A cucurbituril which can be used in the sense of the invention is in principle any compound which is described in the literature as belonging to this class of compound. Included here by definition are the unsubstituted and substituted cucurbiturils described in WO 00/68232 and also the cucurbituril derivatives described in EP-A 1 094 065. Instead of a unitary cucurbituril, substituted cucurbituril or cucurbituril derivative, it is also possible to employ mixtures of two or more such compounds. Where reference is made in the text below to a cucurbituril, and nothing other is expressly stated, the reference is to be understood in the same way as being to a chemically unitary cucurbituril or else to a mixture of two or more cucurbiturils, substituted cucurbiturils and/or cucurbituril derivatives. Correspondingly, quantity figures for cucurbiturils, unless expressly stated otherwise, refer always to the total amount of the one or more cucurbiturils, substituted cucurbiturils and/or cucurbituril derivatives.

Preferred for the purposes of the present invention are cucurbit[n]urils of ring size 5 to 11, and mixtures thereof, particular preference being given to cucurbit[6]uril and also to mixtures containing a predominant fraction of cucurbit[6]uril.

In addition it is possible to use calix[n]arenes of formula (VIII).

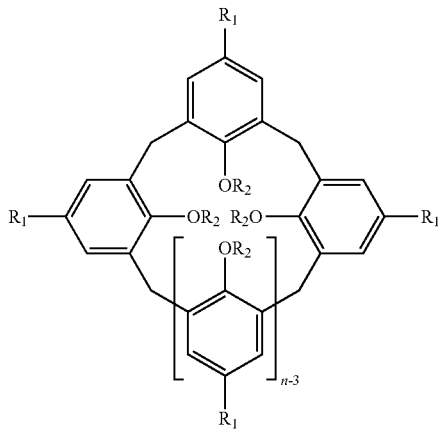

where
$R_1$ is selected from $R_1$=H, alkyl, aryl, alkenyl, alkynyl and also substituted alkyls, aryls, alkenyls, alkynyls which carry groups selected from —OH, —OR', —NH$_2$, —NHR', —NR'R'', NR'R''R'''$^+$, NO$_2$, halogen, SO$_3$H, SO$_3$M (M=alkali metals, alkaline earth metals), carboxylic acids, ketones, aldehydes, amides, esters, —SO$_2$NH$_2$, —SO$_2$NHR, —SO$_2$NR'R'', —SO$_2$halogen, and sulfur-, phosphorus-, and silicon-containing groups and $R_2$ is selected from $R_2$=H, alkyl, aryl, alkenyl, alkynyl and also substituted alkyls, aryls, alkenyls, alkynyls which carry groups selected from —OH, —OR', —NH$_2$, —NHR', —NR'R'', —NR'R''R'''$^+$, —NO$_2$, halogen, —SO$_3$H, —SO$_3$M (M=alkali metals, alkaline earth metals), carboxylic acids, ketones, aldehydes, amides, esters, —SO$_2$NH$_2$, —SO$_2$NHR, —SO$_2$NR'R'', —SO$_2$halogen, and sulfur-, phosphorus-, and silicon-containing groups, R', R'', and R''' independently of one another being selected from H, alkyl, aryl, alkenyl, alkynyl, substituted alkyls, aryls, alkenyls, alkynyls.

Preference is given here to calixarenes of the formula (VIII) for which:

$R_1$ is selected from $R_1$=H, alkyl, aryl, alkenyl, alkynyl and also substituted alkyls, aryls, alkenyls, alkynyls which carry groups which are selected from —OH, —OR', —NH$_2$, —NHR', —NR'R'', NR'R''R'''$^+$, NO$_2$, halogen, SO$_3$H, carboxylic acids, ketones, aldehydes, amides, esters, —SO$_2$NR'R'' and $R_2$ is selected from $R_2$=H, alkyl, aryl, alkenyl, alkynyl and also substituted alkyls, aryls, alkenyls, alkynyls which carry groups which are selected from —OH, —OR', —NH$_2$, —NHR', —NR'R'', —NR'R''R'''$^+$, —NO$_2$, halogen, —SO$_3$H, carboxylic acids, ketones, aldehydes, amides, esters, —SO$_2$NR'R'', R', R'', and R''' independently of one another being selected from H, alkyl, aryl, alkenyl, alkynyl and also substituted alkyls, aryls, alkenyls, alkynyls.

Preferred for the purposes of the present invention are calix[n]arenes of ring size n=4 to 12, and also mixtures thereof, particular preference being given to calix[6]arenes and calix[4]arenes and also to mixtures containing a predominant fraction of calix[6]arenes and/or calix[4]arenes.

Use is to be made, furthermore, of calix[n]resorcarenes, also known as resorcinarenes, of formula IX. N here indicates the number of chain members and can be 4 or 6.

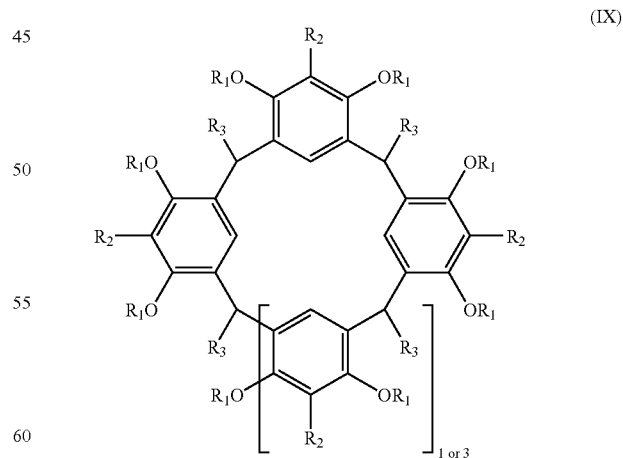

where $R_1$, $R_2$, and $R_3$ are selected from:
$R_1$=H, alkyl, aryl, alkenyl, alkynyl, and also substituted alkyls, aryls, alkenyls, alkynyls which carry groups selected from —OH, —OR, —NH$_2$, —NHR', —NR'R'', NR'R''R'''$^+$, —NO$_2$, halogen, SO$_3$H, SO$_3$M (M=alkali metals, alkaline earth metals), carboxylic acids, ketones, aldehydes, amides, esters, $SO_2NH_2$, $SO_2NHR$, $SO_2NR_2$, $SO_2$halogen, sulfur-, phosphorus-, and silicon-containing groups and $R_2$ and $R_3$ are selected independently of one another from $R_2$, $R_3$=H, alkyl, aryl, alkenyl, alkynyl, and also substituted alkyls, aryls, alkenyls, alkynyls which carry groups selected from —OH, —OR, —$NH_2$, —NHR, NR'R", NR'R"R"'+, —$NO_2$, halogen, —$SO_3H$, —$SO_3M$ (M=alkali metals, alkaline earth metals), carboxylic acids, ketones, aldehydes, amides, esters, —$SO_2NH_2$, —$SO_2NHR$, —$SO_2NR_2$, —$SO_2$halogen, sulfur-, phosphorus-, and silicon-containing groups and R', R", and R"' independently of one another being selected from H, alkyl, aryl, alkenyl, alkynyl and also substituted alkyls, aryls, alkenyls, alkynyls.

Preference is given to calix[4]resorcarenes and/or calix[6]resorcarenes of formula (IX) for which it is the case that $R_1$ is selected from $R_1$=H, alkyl, aryl, alkenyl, alkynyl and also substituted alkyls, aryls, alkenyls, alkynyls which carry groups which are selected from —OH, —OR', —$NH_2$, —NHR', —NR'R", NR'R"R"'+, $NO_2$, halogen, $SO_3H$, carboxylic acids, ketones, aldehydes, amides, esters, —$SO_2NR'R"$ and $R_2$, $R_3$ independently of one another are selected from $R_2$, $R_3$=H, alkyl, aryl, alkenyl, alkynyl and also substituted alkyls, aryls, alkenyls, alkynyls which carry groups which are selected from —OH, —OR', —$NH_2$, —NR'R", —NR'R"R"'+, —$NO_2$, halogen, —$SO_3H$, carboxylic acids, ketones, aldehydes, amides, esters, —$SO_2NR'R"$ R', R", and R"' independently of one another being selected from H, alkyl, aryl, alkenyl, alkynyl and also substituted alkyls, aryls, alkenyls, alkynyls.

It is particularly preferred if $R_2$ is =$R_3$, i.e., $R_2$ and $R_3$ represent the same substituents.

According to a further embodiment the carrier-bound forms of the active substances are present in an amount up to 50% by weight, preferably in an amount of 1% to 20% by weight, and in particular in an amount of 5% to 15% by weight.

Construction Materials and Construction Auxiliaries

The inventively treated construction materials or construction auxiliaries are preferably selected from adhesive bonding, sealing, filling and painting compositions, adhesives, plastics, varnishes, paints, render, mortar, screed, concrete, insulating materials, and primers. Particularly preferred construction materials or construction auxiliaries are joint-sealing compounds (silicone-containing joint sealing compounds, for example), wallpaper pastes, plaster, especially wall plaster and tile plaster, carpet fixatives, silicone adhesives, paints, especially masonry paints, interior wall paints and/or emulsion paints, coating materials for interior and/or exterior, and tile adhesives.

Sealing compounds, and joint-sealing compounds in particular, typically comprise organic polymers and also, in many cases, mineral or organic fillers and other additives.

Examples of suitable polymers are thermoplastic elastomers as described in DE-A-3602526, preferably polyurethanes and acrylates. Suitable polymers are also specified in laid-open specifications DE-A-3726547, DE-A-4029504 and DE-A-4009095, and also in DE-A-19704553 and DE-A-4233077, hereby incorporated in their entirety by reference.

In accordance with the invention the treatment of the sealants of the invention may take place either in the uncured state or in the state cured at below 60° C. Sealants in the context of the invention are materials in accordance with DIN EN 26927, particularly those which cure plastically or elastically as sealing materials. The sealants of the invention can comprise all of the additives that are typical for the corresponding sealing compounds, such as, for example, typical thickeners, reinforcing fillers, crosslinkers, crosslinking catalysts, pigments, adhesion agents or other volume extenders. The actives to be used can be incorporated by dispersing in a manner familiar to the skilled worker, such as, for example, through the use of dispersing equipment, compounders, planetary mixers, etc., in the absence of moisture and oxygen, and incorporation may take place either into the completed sealants or else into parts of these sealants and/or together with one or more components of the sealants.

Even the treatment of ready-cured, crosslinked sealant surfaces can be carried out by applying solutions or suspensions of the substance used in accordance with the invention, the active being transported by swelling or diffusion into the sealant.

Sealants useful in accordance with the invention may be produced either on a silicone, urethane or acrylic basis or, for instance, on an MS polymer basis. Urethane-based sealants are disclosed for example in Ullmann's Encyclopedia of Industrial Chemistry (6th Edition 2003, Chapter 4) and also U.S. Pat. No. 4,417,042. Silicone sealants are known to the skilled worker, as for example from EP 0 118 030 A, EP 0 316 591 A, EP 0 327 847 A, EP 0 553 143 A, DE 195 49 425 A, and U.S. Pat. No. 4,417,042. Examples of acrylic sealants are disclosed inter alia in WO 01/09249 or U.S. Pat. No. 5,077,360. Examples of MS polymer-based sealants are disclosed for example in EP 0 824 574, U.S. Pat. No. 3,971,751, U.S. Pat. No. 4,960,844, U.S. Pat. No. 3,979,344, U.S. Pat. No. 3,632,557, DE 4029504, EP 601 021 or EP 370 464.

In one particularly preferred embodiment the joint-sealing compound is a silicon-based joint-sealing compound, selected in particular from acetate silicones, alkoxy silicones, oxime silicones, benzamide silicones, and amine silicones. As polyorganosiloxanes and as organosilicone compounds with hydrolysable groups, the joint-sealing compound in this context preferably comprises compounds of the kind described in U.S. Pat. No. 5,378,406 in the quantities indicated therein, the disclosure content of said patent in this respect being hereby made part of the subject matter of the present patent specification.

Particular preference is given to systems which crosslink at room temperature, as described for example in EP 0 327 847 or U.S. Pat. No. 5,077,360. These may be one-component or multicomponent systems, with it being possible in the multicomponent systems for catalyst and crosslinker to be present separately (disclosed for example in U.S. Pat. No. 4,891,400 and U.S. Pat. No. 5,502,144), or other so-called silicone RVT 2K systems, especially platinum-free systems.

Particular preference is given to what are called one-component systems, which include all of the ingredients for the construction of a sealing compound, are stored in the absence of atmospheric humidity and/or atmospheric oxygen, and cure at the site of use under reaction with the atmospheric humidity. Particular preference is given to the so-called silicone neutral systems, in which the reaction of crosslinkers with the water in the ambient air does not lead to corrosive, acidic, basic or intensely odorous elimination products. Examples of such systems are disclosed in DE 195 49 425, in U.S. Pat. No. 4,417,042 or in EP 0 327 847.

The sealing compounds, and especially joint-sealing compounds, may comprise aqueous or organic solvents. Suitable organic solvents include hydrocarbons such as cyclohexane, toluene or else xylene or petroleum ethers. Further solvents are ketones such as ethyl butyl ketone or chlorinated hydrocarbons.

In addition it is possible for the sealants to comprise rubberlike polymers as well. Suitable in this case are relatively low molecular mass, commercially customary grades of polyisobutylene, polyisoprene or else polybutadiene-stryene. The use of degraded natural rubber or of neoprene rubber as well is also possible. In this case it is also possible to employ grades which are still fluid at room temperature, and which are frequently referred to as "liquid rubber".

The sealants of the invention can be used in order to seal or interconnect any of a very wide variety of materials. Consideration is given here primarily to their use on concrete, on glass, on plaster and/or enamel and also ceramic and porcelain. Also possible, however, is the joining and/or sealing of moldings and/or profiles made of aluminum, steel or zinc or else of plastics such as PVC or polyurethanes or acrylic resins. Mention may be made, finally, of the sealing of wood or wood materials to any of a very wide variety of other materials.

The consistency of joint-sealing compounds is generally achieved through the addition of finely divided solids, also called fillers. They may be differentiated into organic fillers and inorganic fillers. As inorganic fillers preference may be given, for example, to silica/silicon dioxide (coated or uncoated), chalk—coated or uncoated—and/or zeolites. The latter may also function, moreover, as drying agents. An example of a suitable organic filler is PVC powder. In general, the fillers make a substantial contribution to the possession by the sealant of a necessary internal cohesion after application, thereby preventing the running or bulging of the sealant from vertical joints. The stated adjuvants and fillers can be divided into pigments and thixotropic fillers, also referred to abbreviatedly as thixotropic agents.

Suitable thixotropic agents are the known thixotropic agents such as Bentones, kaolins or else organic compounds such as hydrogenated castor oil and/or derivatives thereof with polyfunctional amines, or the reaction products of stearic acid or ricinoleic acid with ethylenediamine. The concomitant use of silica, particularly of silica from pyrolysis, has proven particularly advantageous. Further suitable thixotropic agents include substantially swellable polymer powders. Examples of such are polyacrylonitrile, polyurethane, polyvinyl chloride, polyacrylic esters, polyvinyl alcohols, polyvinyl acetates, and the corresponding copolymers. Particularly good results can be obtained with finely divided polyvinyl chloride powder. Besides the thixotropic agents it is also possible additionally to use adhesion promoters such as mercaptoalkylsilane, for instance. Here it has proven appropriate to use a monomercaptoalkyltrialkoxysilane. A commercially customary example is mercaptopropyltrimethoxysilane.

The properties of the joint-sealing compound can be improved still further if additional components are added to the polymeric powder used as thixotropic agent. The components in question are substances which fall within the category of the swelling assistants or swelling agents or plasticizers that are employed for plastics.

Suitable examples include plasticizers, particularly for the urethane-based and/or acrylic-based sealants, from the class of the phthalic esters. Examples of compounds that can be employed from this class of substance are dioctyl phthalate, dibutyl phthalate, and benzyl butyl phthalate. Further suitable classes of substance are chlorinated paraffins, alkylsulfonic esters, of the phenols or cresols, for instance, and fatty acid esters.

Highly suitable plasticizers for the silicone sealants are silicone oils, more preferably polydimethylsiloxanes, and also hydrocarbons and/or mixtures thereof, especially hydrocarbons and/or mixtures thereof having a boiling point of greater than 200° C., in particular greater than 230° C.

As swelling assistants it is possible to use those low molecular mass organic substances which are miscible with the polymer powder in the plasticizer. Swelling assistants of this kind can be found in the relevant plastics and polymer handbooks for the skilled worker. Serving as preferred swelling assistants for polyvinyl chloride powders are esters, ketones, aliphatic hydrocarbons, aromatic hydrocarbons, and also aromatic hydrocarbons with alkyl substituents.

Pigments and dyes used are the substances known for these utilities, such as titanium dioxide, iron oxides, and carbon black.

In order to improve the storage stability, the sealants are admixed, as is known, with stabilizers such as benzoyl chloride, acetyl chloride, methyl toluenesulfonate, carbodiimides and/or polycarbodiimides. Olefins having 8 to 20 carbon atoms have proven particularly good stabilizers. Besides the stabilizing effect, they may also fulfill functions of plasticizers and/or swelling assistants. Preference is given to olefins having 8 to 18 carbon atoms, particularly if the double bond is in 1,2 position. The best results are obtained if the molecular structure of these stabilizers is linear.

Another preferred embodiment of the present invention are wallpaper adhesives comprising actives or active combinations of the invention, especially wallpaper pastes comprising aqueous solutions of hydrocolloids such as methylcellulose, methylhydroxypropylcellulose or water-soluble starch derivatives. Aqueous dispersions of film-forming compounds of high molecular mass such as polyvinyl acetate, as well, can be used, especially in conjunction with the aforementioned cellulose derivatives and starch derivatives.

As filter media it is possible to use all known kinds, provided they are suitable for use in water or air filter units. Mention may be made in particular of filter materials of cellulose, glass fibers, PVC fibers, polyester fibers, polyamide fibers, especially nylon fibers, nonwovens, sinter materials, and membrane filters.

Fungi

The fungi which are killed by the azoles, inhibited in their asexual reproduction by the sporulation inhibitors and/or hindered from attaching by the antiadhesive substances are preferably selected from human-pathogenic species of the classes Ascomycota, Basidiomycota, Deuteromycota, and Zygomycota, and more particularly from all species of the genera *Aspergillus, Penicillium, Cladosporium*, and *Mucor*, from the human-pathogenic forms of *Candida*, and also *Stachybotrys, Phoma, Alternaria, Aureobasidium, Ulocladium, Epicoccum, Stemphyllium, Paecilomyces, Trichoderma, Scopulariopsis, Wallemia, Botrytis, Verticillium*, and *Chaetonium*.

The Ascomycota here include, in particular, all species of the genera *Aspergillus, Penicillium*, and *Cladosporium*. These fungi form spores which on contact with the skin or the airways have a strong allergy-triggering potential. The Basidiomycota include, for example, *Cryptococcus neoformans*. The Deuteromycota include all of the genera known as mold fungi, particularly those which owing to the absence of a sexual stage are not counted among the classes of the Ascomycota, Basidiomycota or Zygomycota.

With particular preference the fungi are species of the generus *Aspergillus*, more particularly species selected from *Aspergillus aculeatus, Aspergillus albus, Aspergillus alliaceus, Aspergillus asperescens, Aspergillus awamori, Aspergillus candidus, Aspergillus carbonarius, Aspergillus carneus, Aspergillus chevalieri, Aspergillus chevalieri* var. *intermedius, Aspergillus clavatus, Aspergillus ficuum, Aspergillus flavipes, Aspergillus flavus, Aspergillus foetidus,*

*Aspergillus fumigatus, Aspergillus giganteus, Aspergillus humicola, Aspergillus intermedius, Aspergillus japonicus, Aspergillus nidulans, Aspergillus niger, Aspergillus niveus, Aspergillus ochraceus, Aspergillus oryzae, Aspergillus ostianus, Aspergillus parasiticus, Aspergillus parasiticus* var. *globosus, Aspergillus penicillioides, Aspergillus phoenicis, Aspergillus rugulosus, Aspergillus sclerotiorum, Aspergillus sojae* var. *gymnosardae, Aspergillus sydowi, Aspergillus tamari, Aspergillus terreus, Aspergillus terricola, Aspergillus toxicarius, Aspergillus unguis, Aspergillus ustus, Aspergillus versicolor, Aspergillus vitricolae*, and *Aspergillus wentii*, very particular preference being given to *Aspergillus flavus* and *Aspergillus nidulans*.

WORKING EXAMPLES

Microbiological Assessment

A)

The microbiological assessment for distinguishing the long-term inhibition of mold growth by cured silicone sealant formulations is possible with the following methods:

A1 Aging of the Silicone Compounds in the QUV Accelerated Weathering Apparatus

Cured silicone films (approximately 80×60×5 mm) are sprayed alternately for 15 minutes each with a spray solution (2% strength aqueous Texapon NSO solution containing 0.5% Dehydran 1513 defoamer), then irradiated with UV light for 15 minutes, in a QUV accelerated weathering instrument (e.g. QUV-spray model). Per week, the test specimens are exposed to 198 spraying units and 198 UV units. After 4 (792 shower cycles), 8 (1584 shower cycles), and 12 weeks (2376 shower cycles), test specimens are taken for microbiological examination. An unweathered sample is likewise investigated microbiologically.

A2 Microbiological Test: Realistic Test for Film Preservation along the Lines of DIN EN ISO846

The fungal resistance of cured joint-sealing compounds is assessed in a method based on DIN EN ISO846: "Determination of the action of microorganisms on plastics (ISO 846: 1997 German version EN ISO 846: 1997); (amended).

Test specimens of cured joint-sealing compounds are applied planarly to an agar surface. A fungal suspension is caused to act on the test specimens and the surrounding agar surface. After incubation, an assessment is made of the growth on and around the test specimens.

Test conditions: The following important amendments and additions to the DIN EN ISO 846 are carried out:
(1) The test specimens are tested to DIN EN ISO 846 without pretreatment. Additionally, test specimens are also assessed in the test after pretreatment. This pretreatment (leaching) may take place, for example, by incubation for a number of weeks in a flow-traversed immersion bath with water or by accommodating suitable test specimens in a QUV;
(2) The fungal spore suspension is incubated under relatively harsh, realistic conditions with increased ambient air humidity (approximately 85% relative humidity) in a humid chamber;
(3) The test specimens are incubated on 'complete nutrient medium' (cf. DIN EN ISO 846 4.2.1.2 method B), but with 'wort agar';
(4) As test organisms use is made either of the test fungi envisaged in DIN EN ISO 846:
*Aspergillus niger* ATCC 6275
*Penicillium funiculosum* ATCC 36839
*Paecilomyces variotii* ATCC 18502
*Gliocladium virens* ATCC 9645
*Chaetomium globosum* ATCC 6205
or, alternatively, the strain *Aspergillus niger* (ATCC 6275) as sole test organism.

Evaluation of the growth on the test elements:
0=no growth visible under microscope viewing
1=no growth visible with naked eye, but growth clearly visible under the microscope
2=growth visible with naked eye, up to 25% of the sample surface overgrown
3=growth visible with naked eye, up to 50% of the sample surface overgrown
4=considerable growth, over 50% of the sample surface overgrown
5=severe growth, entire sample surface overgrown All in all, the specimens are incubated for 18 weeks and inoculated again after 4 and 8 weeks in each case. The individual evaluations are added over this period and reported collectively as the infestation index.

B) Antiadhesive Activity

As an example, the demonstration of the antiadhesive activity of nonionic surfactants following incorporation into joint-sealing compositions is described.

The sealant used was the silicone sealant DC3390. 1% by weight of surfactant was added and the composition was homogenized in a Speedmixer. The nonionic surfactants incorporated into the joint-sealing composition were $C_9$-alkylphenyl-$(EO)_9$ (Disponil NP9, Cognis), $C_{12}$-$C_{14}$ alkyl-$(EO)_5$-$(PO)_4$ (Dehypon LS54, Cognis), and $F(CF_2CF_2)_{1-7}$—$CH_2CH_2O(CH_2CH_2O)_{1-15}H$ (Zonyl FSO 100, DuPont), and they were compared with joint-sealing compounds without added surfactant. The compound obtained was spread out as a film (22×22×2 mm) and left to cure in the air. The test element obtained in this way was disinfected with 70% ethanol for 10 minutes, then washed with distilled water and dried. Subsequently the test elements were overlaid with a microbial suspension of *Aspergillus niger* and incubated for one hour. Thereafter the microbial suspension was withdrawn under suction, and the test element was washed twice. Following transfer of the test elements into sterile 6-well plates, the microbe carriers were overlaid with wort agar+INT. Subsequently, after 48 hours of incubation at 25° C., the number of colony-forming units (CFU) was ascertained. Through the use of nonionic surfactants, and especially when using fluorinated nonionic surfactants, a distinct reduction is achieved in the number of colony-forming units.

C) Sporulation Inhibition Activity

As an example, the demonstration of the inhibition of asexual reproduction by ortho-phenylphenol and ortho-phenylphenol-silicic ester in joint-sealing compounds is described.

The surface of wort agar plates was contaminated with 100 μl in each case of a microbial suspension ($10^3$ CFU/ml) of *Aspergillus niger* (DSM1988). Added beforehand to the agar plates were different amounts of active (solutions in ethanol, for final concentrations see table). The plates were incubated at 25° C. for 3 days. Spore formation was assessed visually and the sporulation rate was ascertained in [%]. The concentrations of active employed did not hinder the growth of the test strain, except where indicated in the tables below. A growth inhibition or microbicidal effect only occurred for a concentration of 0.05% by weight OPP. Spore formation was completely suppressed, however, at an OPP concentration which was fifty times lower, without any growth inhibition activity occurring.

TABLE 1 ortho-phenylphenol

| | Concentration of OPP [%] | | | | | | | | |
|---|---|---|---|---|---|---|---|---|---|
| | 0 | 0.00001 | 0.00005 | 0.0001 | 0.0005 | 0.001 | 0.005 | 0.05 | 0.1 | 1.0 |
| Sporulation [%] | 100 | 95 | 95 | 95 | 50 | 25 | 0 | no growth | no growth | no growth |

Spore formation was inhibited with increasing concentrations and suppressed completely at a use concentration of 0.001% by weight.

TABLE 2 ortho-phenylphenol-silicic ester

| | Concentration of OPP-silicic ester [%] | | | | | | | |
|---|---|---|---|---|---|---|---|---|
| | 0 | 0.00001 | 0.00005 | 0.0001 | 0.0005 | 0.001 | 0.005 | 0.01 |
| Sporulation [%] | 100 | 95 | 95 | 95 | 50 | 25 | 0 | 0 |

Spore formation was inhibited with increasing concentrations and suppressed completely at a use concentration of 0.005% by weight.

D) Fungicidal Activity of Azole Derivatives

As an example of the fungicidal activity of azole derivatives, the demonstration of the fungicidal action of tebuconazole in joint-sealing compositions is described. For the purpose of comparison, the use of the conventionally used fungicide, DCOIT, was tested.

A commercially customary silicone joint sealant (e.g., Dow Corning 3390) is admixed with the actives described and stirred with a stirrer until homogeneity is achieved. Thereafter, films of the sealant are produced and tested as described above.

| Active | Amount of active added | Infestation index |
|---|---|---|
| — | — | 80 |
| DCOIT | 500 ppm | 77 |
| | 1000 ppm | 81 |
| | 2000 ppm | 78 |
| Tebuconazole | 500 ppm | 60 |
| | 1000 ppm | 57 |
| | 2500 ppm | 37 |
| | 5000 ppm | 20 |
| | 10000 ppm | 12 |

Formula Examples for Wallpaper Pastes

| Ingredients | Amount |
|---|---|
| Methylhydroxyethylcellulose (300 m · Pas in 2% strength aqueous solution, methoxy content 26%) | 500 g |
| PVAcetate redispersible powder | 350 g |
| Kaolin | 60 g |
| Cellulose powder | 50 g |
| Adduct of 6 mol of ethylene oxide with 1 mol of nonylphenol | 10 g |
| Commercially customary preservative (based on isothiazoline derivative) | 8 g |
| ortho-Phenylphenol | 0.1 g |
| Tebuconazole | 5 g |
| Eumulgin B1 | 1 g |

| Ingredients | Amount |
|---|---|
| Methylhydroxyethylcellulose (5000 m · Pas in 2% aqueous solution, methoxy content 19%) | 680 g |
| Carboxymethyl starch (DS 0.22) | 300 g |
| Adduct of 4 mol of ethylene oxide with 1 mol of fatty alcohol | 15 g |
| Commercially customary preservative (based on isothiazoline derivative) | 10 g |
| ortho-Phenylphenol | 0.1 g |
| Tebuconazole | 5 g |
| Eumulgin B1 | 1 g |

| Ingredients | Amount |
|---|---|
| Commercially customary polyvinyl acetate dispersions (50% solids content) | 500 g |
| Water | 200 g |
| Methylhydroxyethylcellulose (3000 m · Pas in 2% aqueous solution) | 20 g |
| Commercially customary preservative | 10 g |
| ortho-Phenylphenol | 0.1 g |
| Tebuconazole | 5 g |
| Eumulgin B1 | 1 g |

The mixtures obtained are prepared by stirring with water in a ratio of 1:20 (2) or 1:25 (3) or 1:1 (4) and are used for sticking commercially customary wallpapers to wall surfaces.

As used herein, and in particular as used herein to define the elements of the claims that follow, the articles "a" and "an" are synonymous and used interchangeably with "at least one" or "one or more," describing or including both the singular and the plural, unless specifically defined otherwise. The conjunction "or" is used herein, such that phrases formed by terms conjoined by "or" describe or include each term alone as well as any combination of terms so conjoined, unless specifically defined otherwise. All numerical quantities are understood to be modified by the word "about," unless specifically defined otherwise or unless an exact amount is needed to define the invention over the prior art.

What is claimed is:

1. A material comprising a filter medium, construction material, construction auxiliary, textile, pelt, paper, hide or leather, and 0.1 to 1% by weight of at least one azole compound selected from one or more of propiconazole, tebuconazole, and their derivatives, 0.0001 to 0.05% by weight of at least one sporulation inhibitor selected from ortho-phenylphenol or an ortho-phenylphenol-silicic ester, and 0.001 to 10% by weight of at least one antiadhesive substance comprising a silicic ester of a $C_8$ to $C_{22}$ fatty alcohol adduct with 3 to 15 units of ethylene oxide; wherein the azole compound, the sporulation inhibitor and the antiadhesive substance are present in amounts that achieve a synergistic effect against mold.

2. The material of claim 1, wherein the sporulation inhibitor is ortho-phenylphenol.

3. The material of claim 1, comprising 0.01% to 2% by weight of the antiadhesive substance.

4. The material of claim 1, comprising 0.2% to 0.6% by weight of the azole compound, 0.001% to 0.05% by weight of the sporulation inhibitor, and 0.05% to 1.0% by weight of the antiadhesive substance.

5. The material of claim 1, wherein the azole:sporulation inhibitor ratio is in the range of 1:0.0001 to 1:0.5.

6. A method of inhibiting mold-related discoloration, comprising the steps of providing a material selected from the group consisting of construction materials, construction auxiliaries, filter media, textiles, pelts, paper, hides, and leather, and providing said material with an azole compound selected from one or more of propiconazole, tebuconazole, and their derivatives in an amount of about 0.1 to 1% by weight, a sporulation inhibitor selected from ortho-phenylphenol or an ortho-phenylphenol-silicic ester in an amount of about 0.0001 to 0.05% by weight, and an antiadhesive substance comprising a silicic ester of a $C_8$ to $C_{22}$ fatty alcohol adduct with 3 to 15 units of ethylene oxide in an amount of about 0.001 to 10% by weight, wherein said amounts are synergistically effective to inhibit mold-related discoloration of said material.

7. The method of claim 6, wherein the construction material or construction auxiliary is selected from the group consisting of bonders, sealants, fillers, coatings, adhesives, plastic, varnish, paint, render, mortar, screed, concrete insulation, and primers.

8. The method of claim 6, wherein the material is provided with 0.1% to 1% by weight of the azole compound, 0.0001% to 0.05% by weight of the sporulation inhibitor, and 0.01% to 2% by weight of the antiadhesive substance.

* * * * *